United States Patent
Schmidt

(10) Patent No.: US 6,569,077 B2
(45) Date of Patent: May 27, 2003

(54) DIMPLED SEED IMPLANT NEEDLE

(76) Inventor: Bruno Schmidt, 100 Cunningham Dr., New Smyrna Beach, FL (US) 32168

( * ) Notice: Subject to any disclaimer, the term of this patent is extended or adjusted under 35 U.S.C. 154(b) by 0 days.

(21) Appl. No.: 09/902,006

(22) Filed: Jul. 11, 2001

(65) Prior Publication Data

US 2003/0013934 A1 Jan. 16, 2003

(51) Int. Cl.[7] .......................... A61M 36/00; A61N 5/00
(52) U.S. Cl. ............................................................ 600/7
(58) Field of Search ........................ 600/7, 1–6; 606/59, 606/60

(56) References Cited

U.S. PATENT DOCUMENTS

| | | | | |
|---|---|---|---|---|
| 4,105,030 A | * | 8/1978 | Kercso .................. | 604/506 |
| 4,263,910 A | * | 4/1981 | Pardekooper et al. ......... | 604/60 |
| 5,281,197 A | * | 1/1994 | Arias et al. ................ | 604/209 |
| 5,395,319 A | * | 3/1995 | Hirsch et al. .............. | 604/264 |
| 5,810,769 A | * | 9/1998 | Schlegel et al. ............ | 604/104 |
| 5,827,293 A | * | 10/1998 | Elliott ........................ | 600/7 |
| 6,402,677 B1 | * | 6/2002 | Jacobs ........................ | 600/7 |

FOREIGN PATENT DOCUMENTS

FR 2432456 A * 4/1980 .......... A61M/37/00

* cited by examiner

*Primary Examiner*—Max F. Hindenburg
*Assistant Examiner*—Jonathan Foreman
(74) *Attorney, Agent, or Firm*—Stanley M. Miller

(57) ABSTRACT

A seeding needle has a detent formed near its distal end to prevent radioactive seeds and spacers from sliding out of the needle under the influence of gravity. In a first embodiment, the detent is provided in the form of a dimple that provides an interior protuberance that holds the seeds and spacers and a smooth exterior recess that does not cut tissue as the needle is advanced or retracted. In a second embodiment, a coined slot provides an interior protuberance and an exterior recess also having smooth, non-cutting edges. A third embodiment provides a plug that enables reduction of the size of the detent.

1 Claim, 2 Drawing Sheets

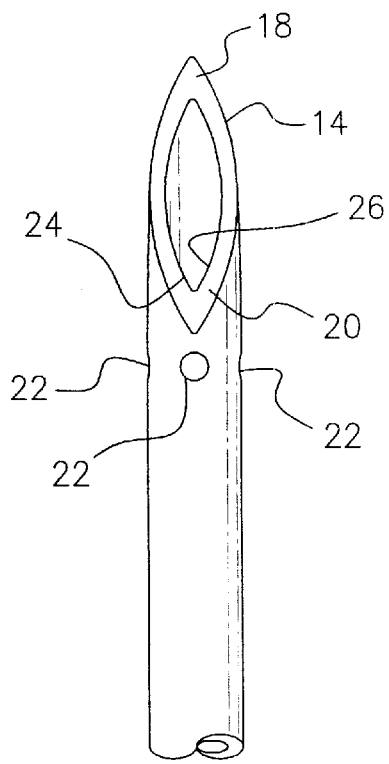
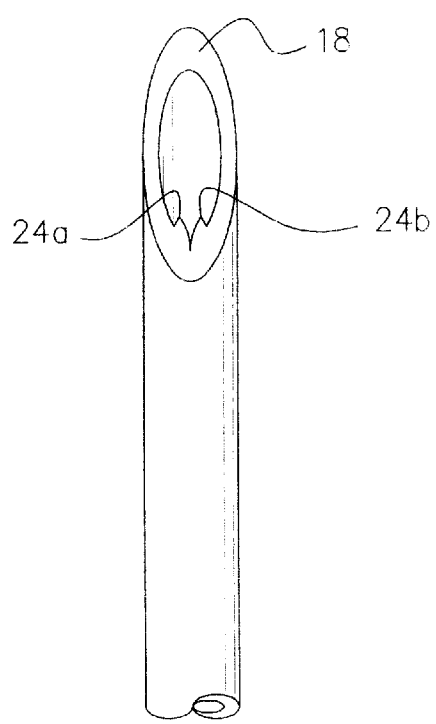
FIG. 4    FIG. 5
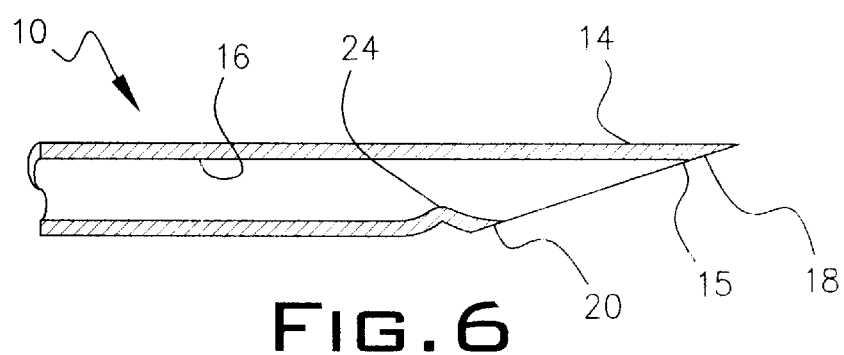
FIG. 6
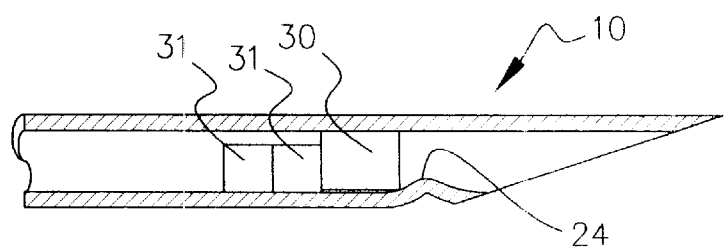
FIG. 7

DIMPLED SEED IMPLANT NEEDLE

BACKGROUND OF THE INVENTION

1. Field of the Invention

This invention relates, generally, to needles of the type used to implant radioactive seeds. More particularly, it relates to a prostate seeding needle having means for encapsulating seeds and spacers within the lumen of the needle.

2. Description of the Prior Art

Seeding needles are used to position radioactive seeds in tumors within the body. Although this invention relates to a seeding needle used to implant radioactive seeds within a prostate gland, it has utility in other applications as well and this invention is not limited to prostate seeding needles only.

Typically, non-radioactive spacers are also positioned in the lumen of a seeding needle, together with the radioactive seeds. However, the spacers have the same general size and shape as the seeds and therefore they may be treated as seeds from a mechanical standpoint.

Bone wax is currently used to plug the distal end or tip of the needle to prevent the seeds and spacers from sliding out of the lumen. The depth of the bone wax may vary, however, with the result that it is difficult for the physician to locate the first seed with precision. For example, if excessive bone wax is used to plug the distal end, the first seed will be further from the tip of the needle than it would have been if the correct amount of bone wax had been used. Similarly, if an inadequate amount of bone wax is used, the first seed will be closer to the tip of the needle than it should have been.

More particularly, in the conventional method of positioning and deploying the radioactive seeds, the needle has a specially treated echogenic tip, extending 2–7 mm back from the needle point. Sound waves bounce off the echogenic tip and thus provide to the physician real-time knowledge as to the location of the needle point. The echogenic tip is inserted into the prostate gland and moved back and forth until it is positioned properly according to an ultrasound device that registers only the position of the echogenic tip. The stylet is then pushed down the lumen of the needle until the physician encounters the resistance of the seeds and spacers against the bone wax. The stylet is then held stationary and the needle is withdrawn over the seeds and spacers, thereby leaving the first seed in very close proximity to the position of the echogenic tip as determined by the ultrasound. It is very important that the first seed be positioned in very close proximity to the echogenic tip because the seeds cannot be recaptured and repositioned after they are deployed.

One prior art device that does not employ bone wax is owned by U.S. Biopsy, Inc. A "U"-shaped cut is formed in the needle near its distal end, approximately 7 mm from the tip of the needle, and the metal bordered on three sides by the cut is pushed into the interior of the needle. This piece of metal acts as a detent means within the lumen and prevents seeds and spacers from exiting the tip of the needle under the influence of gravity. The detent is resilient and flexible so that it can be pushed out of the way when a physician applies force to a stylet that is inserted into the lumen from the proximal end thereof. To discharge a seed from the lumen, the needle is withdrawn while the stylet is maintained in position.

This detent means eliminates the need for bone wax and ensures that the first seed will always be the same distance from the tip of the needle. However, when the "U"-shaped cut out is formed in the needle, a "U"-shaped hollow is formed in the surface of the needle and that hollow is bordered by a "U"-shaped sharp edge. Tissue enters into the hollow and can be cut by the positioning action of the needle. This unwanted cutting causes trauma to the patient and can lead to unwanted complications.

What is needed, then, is a better way to hold seeds and spacers in the lumen of seeding needles prior to use. More particularly, a means is needed that does not employ bone wax and that will position the first seed very close to the echogenic tip of the needle by a precise, uniform distance so that a physician can consistently position the first seed in exactly the correct location.

Moreover, there is a need for a means that does not cause unwanted cutting of tissue when a seeding needle is introduced into a prostate gland or other tissue.

However, in view of the prior art considered as a whole at the time the present invention was made, it was not obvious to those of ordinary skill in the pertinent art how the identified needs could be fulfilled.

SUMMARY OF THE INVENTION

The longstanding but heretofore unfulfilled need for an improvement in seeding needles is now met by a new, useful, and nonobvious seeding needle that includes at least one dimple formed in the needle near a distal end thereof. The dimple or dimples form a recess on an exterior surface of the needle and a protuberance that extends into a lumen of the needle. The protuberance provides a detent means that prevents a radioactive seed from sliding out of the lumen under the influence of gravity. The detent means is flexible and resilient so that a radioactive seed may be displaced past the detent means when sufficient force is applied to the radioactive seed. In a first embodiment, the recess is hemispherical in configuration and has smooth edges to minimize trauma to tissue during insertion and retraction of the needle. Accordingly, the protuberance is also hemispherical in configuration. In a second embodiment, the recess is a coined slot with smooth edges and the protuberance is shaped like a knife blade.

The novel method for forming a detent means in a needle includes the steps of providing a mandrel having a depression or recess of predetermined configuration formed therein. The mandrel is inserted into a lumen of the needle so that the depression to be formed in the mandrel is positioned at a predetermined position. A die having a protuberance of predetermined configuration that is complementary to the predetermined configuration of the depression or recess is provided and is positioned externally of the lumen in registration with the depression or recess formed in the mandrel. The needle is then struck with the die. The predetermined configuration of the depression or recess and the protuberance is hemispherical in the first embodiment. In the second embodiment, the depression or recess has the configuration of a coined slot and the protuberance is shaped like a knife blade.

In a third embodiment, a flexible and resilient plug means is disposed in a lumen of the needle in leading relation to a plurality of seeds and spacers in a seed and spacer string so that the detent means detains the plug means within the lumen, and hence detains the seed and spacer string disposed behind the plug means. The plug means has a diameter slightly greater than a diameter of the seeds and spacers. The detent means merely needs to protrude into the lumen by an amount sufficient to prevent the plug means from sliding therepast under the influence of gravity. The detent means therefore protrudes into the lumen less than the detent means would be required to protrude in the absence of the plug means.

A primary object of the invention is to provide a seeding needle that does not employ bone wax to maintain seed and spacers within the lumen thereof.

Another important object is to provide a bone wax-free seeding needle that does not cut tissue as the needle is positioned within a patient.

Another major object is to provide a method whereby a detent means is consistently formed in a seeding needle in the same position, i.e., at the same distance from the distal end of the needle, very close to the tip.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 4 is a perspective view of a second embodiment;

FIG. 5 is a detailed view depicting how a pair of opposed flaps are folded inwardly into the lumen of the needle when the slot is cut;

FIG. 6 is an enlarged longitudinal sectional view of the second embodiment; and

FIG. 7 is an enlarged longitudinal sectional view of a third embodiment.

DETAILED DESCRIPTION OF THE PREFERRED EMBODIMENT

Figure 1:
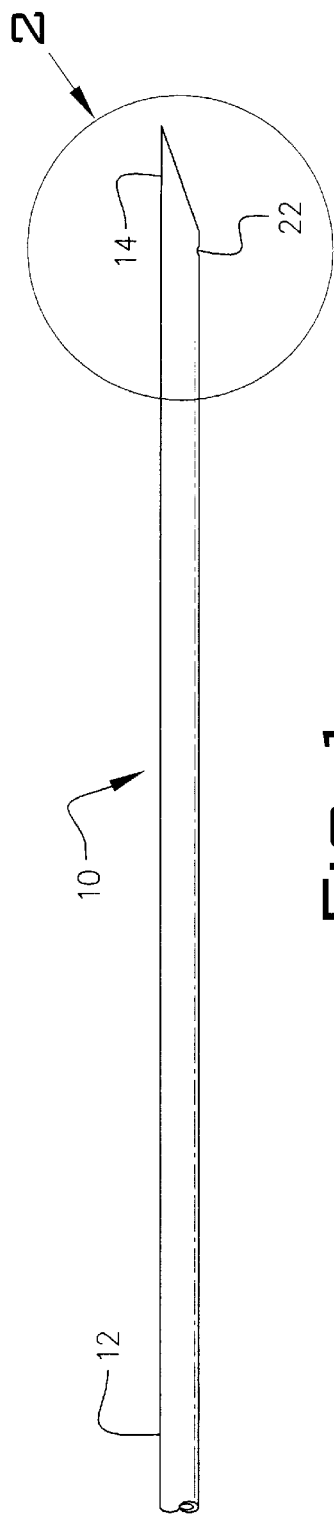
FIG. 1 is a side elevational view of a first embodiment of the novel seeding needle.

Referring now to FIG. 1, it will there be seen that the reference numeral 10 denotes an illustrative embodiment of the present invention.

Seeding needle 10 includes proximal end 12 and sharp distal end 14. The interior of the needle, or lumen, is denoted 16 in FIG. 2. Seeds and spacers typically have a diameter of about 0.032 inch so lumen 16 is a little larger in diameter to slidingly accommodate them.

Distal end 14 is created by making a bevel cut 15 in needle 10 in a well-known way. The distal end of the bevel is denoted 18 and the proximal end of the bevel is denoted 20.

Dimple 22 is preferably formed in needle 10 adjacent the proximal end 20 of bevel 15. Dimple 22 is punched into the needle by any suitable dimple-forming means and no cut is made in the needle. Accordingly, no tissue is cut by the dimple when the needle is advanced into tissue. Each dimple has an exterior surface or recess and an interior surface or protuberance.

The depth of dimple 22 is sufficient to reduce the diameter of lumen 16 to about 0.031 inch or less. Since the seeds and spacers have a slightly larger diameter, dimple 22 acts as a detent and prevents said seeds and spacers from sliding out of the distal end of the needle under the influence of gravity. In this embodiment, the depth of dimple 22 is about 0.008 to 0.010 inch.

Figure 3:
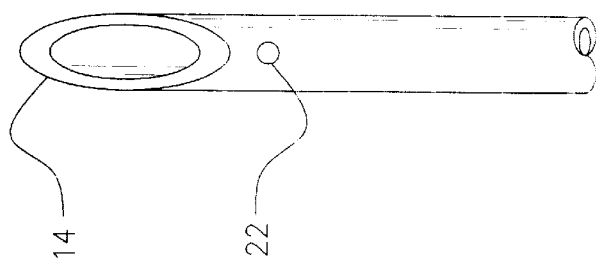
FIG. 3 is a bottom plan view of the distal end of the needle.
Figure 2:
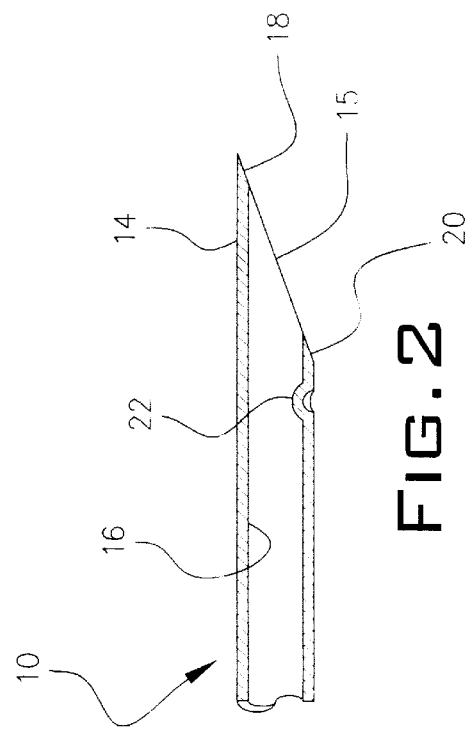
FIG. 2 is an enlarged longitudinal sectional view of the area denoted by reference numeral 2 in FIG. 1.

Dimple 22 need not be positioned in the location depicted in FIGS. 1–3. It may be positioned anywhere about the circumference of the needle. Moreover, more than one dimple may be provided. Where multiple dimples are provided, they may be circumferentially spaced about needle 10 and may be aligned in a common plane that is perpendicular to the longitudinal axis of needle 10.

Seeds and spacers are dispensed from needle 10 in the conventional way. The needle is retracted over a stylet, not shown, that is introduced into lumen 16 from proximal end 12 of the needle. Accordingly, the stylet is positioned on the proximal end of the seeds and spacers. As is well-known, the stylet is maintained in position by the physician as the needle is retracted. The dimple is flexible and resilient. Thus, as the physician exerts a minor amount of force, a seed or spacer is squeezed past the dimple.

FIGS. 4–6 depict an alternative detent means. In this embodiment, a coined slot 24 is formed in needle 10 at the proximal end 20 of bevel cut 15. Like dimple 22, coined slot 24 is free of sharp edges and creates no hollow into which tissue may enter. Coined slot 24 reduces the diameter of lumen 16 to about 0.031 inch or less to provide a detent means. The stylet is used as in the first embodiment to force individual seeds or spacers past the flexible and resilient detent created by coined slot 24.

FIG. 4 also indicates that coined slot 24 may also be employed as the only detent. means, or in conjunction with one or more dimples 22. When both the coined slot and dimples are used, the longitudinal distance between said detent means is equal to the length of a seed or spacer.

FIG. 5 indicates how two opposed flaps 24a, 24b are folded into lumen 16 when coined slot 24 is made. These opposed flaps provide the detent means. They have a common height of about 0.008–0.010 inch and thus protrude into lumen 16 by about the same amount as dimple or dimples 22.

To form dimple 22 or coined slot 24, a mandrel is first inserted into lumen 16 of needle 10. If a dimple is to be formed, a mandrel having a hemispherical recess formed therein is used. If a coined slot is to be formed, a mandrel having a grooved recess formed therein is used. The decrease in diameter of lumen 16 is determined by the depth of the recess or groove formed in the mandrel. A coining die of the desired shape (a rounded protuberance for forming a dimple and a knife blade for forming a groove) is then positioned outside the needle in registration with the rounded or grooved recess and sharply knocked into the needle. In this way, the depth of the recess or groove formed in the mandrel defines the depth of the detent that is formed in the needle when the mandrel is withdrawn. The location of the dimple or coined slot is consistent from needle to needle.

As indicated in FIGS. 4 and 6, when a coined slot is formed, the slot extends longitudinally from heel 26 (the heel being the proximal end of the opening formed by the lumen). This elongates the needle bevel opening as depicted.

Both dimple 22 and coined slot 24 are formed by the same method. To form a dimple, a mandrel having a hemispherical depression formed therein is positioned within lumen 16 so that the depression is positioned where the dimple is desired. A die having a hemispherical protuberance then strikes the needle where the dimple is desired. The mandrel is then withdrawn. Similarly, to form a coined slot, a mandrel having a elongate groove formed therein is positioned within lumen 16 so that the slot is positioned where the coined slot is desired. A die having a blade-like protuberance then strikes the needle where the coined slot is desired and the mandrel is withdrawn.

Both embodiments represent significant improvements in the art. Neither dimple 22 nor coined slot 24 has sharp edges that can cut tissue, yet each provides an effective detent means that is consistently positioned in an optimal position, thereby overcoming the problems associated with bone wax.

A third embodiment is depicted in FIG. 7. A plug 30 having a diameter slightly greater than the common diameter of the seeds and spacers 31 is introduced into the lumen, at the leading (distal) end of the seed and spacer string. Plug 30 could be made of the same material as the spacers so that it is slightly deformable. (Radioactive seeds are formed of titanium and are not deformable). The dimple or dimples or coined slot would therefore block plug 30 and thus block the seed and spacer string 31. When pressure is exerted by the stylet, resilient and flexible plug 30 and the detent means as well momentarily deform and the seed and spacer string deploys, following the plug, with no further obstruction felt by the physician as the seed and spacer string deploys. As mentioned in connection with the first embodiments, the depth of dimple or dimples 22, or the height of opposed flaps 24a, 24b, is about 0.008–0.010 inch. However, with use of plug 30, the depth of the dimple or dimples and the height of the opposed flaps could be decreased. Thus, less striking force per dimple or coined slot is required during the manufacturing process, thereby extending the life of the mandrel and dies and decreasing the per unit cost of the innovative needle. Although FIG. 7 depicts coined slot 24, it should be understood that the detent means could also be provided in the form of a dimple or dimples 22.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described.

What is claimed is:

1. A seeding needle, comprising:

a detent means formed in said needle near a distal end thereof;

said detent means forming a protuberance that extends into a lumen of said needle;

a flexible and resilient plug disposed in a lumen of said needle in leading relation to a plurality of seeds and spacers in a seed and spacer string so that said detent means detains said flexible and resilient plug within said lumen, and hence detains said seed and spacer string disposed behind said plug;

said flexible and resilient plug having a diameter slightly greater than a common diameter of seeds and spacers in said seed and spacer string;

said detent means being flexible and resilient so that said flexible and resilient plug is displaced past said detent means when sufficient force is applied to said flexible and resilient plug;

said protuberance of said detent means protruding into said lumen by an amount sufficient to prevent said flexible and resilient plug from sliding therepast under the influence of gravity;

said detent means protruding into said lumen less than said detent means would be required to protrude in the absence of said flexible and resilient plug.

\* \* \* \* \*